US009144576B2

(12) United States Patent
Brown et al.

(10) Patent No.: US 9,144,576 B2
(45) Date of Patent: *Sep. 29, 2015

(54) TOPICAL ANTIVIRAL FORMULATIONS

(71) Applicant: 3B Pharmaceuticals, Inc., Parker, CO (US)

(72) Inventors: Darby C. Brown, Parker, CO (US); Kristen A. Brown, Parker, CO (US)

(73) Assignee: 3B Pharmaceuticals, Inc., Parker, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/094,061

(22) Filed: Dec. 2, 2013

(65) Prior Publication Data

US 2014/0221297 A1    Aug. 7, 2014

Related U.S. Application Data

(63) Continuation of application No. 13/523,471, filed on Jun. 14, 2012, now abandoned, which is a continuation of application No. 12/572,584, filed on Oct. 2, 2009, now Pat. No. 8,236,768.

(60) Provisional application No. 61/102,729, filed on Oct. 3, 2008.

(51) Int. Cl.
*A61K 31/70* (2006.01)
*A61K 31/7004* (2006.01)
*A61K 9/00* (2006.01)
*A61K 31/522* (2006.01)

(52) U.S. Cl.
CPC ........... *A61K 31/7004* (2013.01); *A61K 9/0014* (2013.01); *A61K 31/522* (2013.01)

(58) Field of Classification Search
CPC .................. A61K 31/7004; A61K 31/522
See application file for complete search history.

(56) References Cited

U.S. PATENT DOCUMENTS

| | | | |
|---|---|---|---|
| 4,315,001 A | 2/1982 | Blough | |
| 4,603,122 A | 7/1986 | Blough | |
| 4,963,555 A | 10/1990 | Jones et al. | |
| 5,585,379 A | 12/1996 | Sintov et al. | |
| 5,658,946 A * | 8/1997 | Majeti | 514/493 |
| 5,658,956 A | 8/1997 | Martin et al. | |
| 5,666,962 A | 9/1997 | Lamey | |
| 6,117,857 A | 9/2000 | Carlsson et al. | |
| 6,193,985 B1 | 2/2001 | Sonne | |
| 6,255,318 B1 | 7/2001 | Bedard et al. | |
| 6,440,980 B1 | 8/2002 | Marcelletti et al. | |
| 6,734,170 B2 | 5/2004 | Petit et al. | |
| 6,936,187 B2 | 8/2005 | Lynch et al. | |
| 6,967,023 B1 | 11/2005 | Eini et al. | |
| 7,091,190 B2 | 8/2006 | Marcelletti et al. | |
| 7,192,607 B2 | 3/2007 | Bergeron et al. | |
| 7,253,175 B2 | 8/2007 | Lieberman et al. | |

| | | |
|---|---|---|
| 2004/0208914 A1 | 10/2004 | Richlin et al. |
| 2006/0088517 A1 | 4/2006 | Kriegler et al. |
| 2006/0287253 A1 | 12/2006 | Kriegler et al. |
| 2008/0293703 A1 | 11/2008 | Richlin et al. |
| 2008/0299220 A1 | 12/2008 | Tamarkin et al. |
| 2009/0118168 A1 | 5/2009 | Dinh et al. |
| 2010/0111883 A1 | 5/2010 | Vitins et al. |
| 2011/0065655 A1 | 3/2011 | Whitten |

FOREIGN PATENT DOCUMENTS

| | | |
|---|---|---|
| WO | WO 93/18763 | 9/1993 |
| WO | WO98/17264 A1 | 4/1998 |
| WO | WO 99/12545 | 3/1999 |
| WO | WO 00/01390 | 1/2000 |

OTHER PUBLICATIONS

Blough and Giuntoli (1979), J. Am. Med. Assoc, 241(26)2798-2801, "Successful Treatment of Human Genital Herpes Infections With 2-Deoxy-D-glucose".

Brusick, "A critical review of the genetic toxicity of steviol and steviol glycosides", Food and chemical Toxicology, 46(7)(sup):S83-S91 (Jul. 2008). Retrieved from the internet <http://www.sciencedirect.com/science/article/pii/S0278691508002354> Dec. 14, 2011, 9 pgs.

Calbiotech Inc., (CBI, Spring Valley, CA, Cat. No. H1029G or H1029G4) HSV-1 ELISA Package Insert.

Calbiotech Inc., (CBI, Spring Valley, CA, Cat. No. H2031G or H2031G4) HSV-2 ELISA Package Insert.

Gennaro, A. R., Remington: The Science and Practice of Pharmacy, 18$^{th}$ Ed., 1990, Mack Publishing Company, vol. II, pp. 1635-1637.

Gennaro, A.R., Remington: Practice of the Science and Pharmacy, 19$^{th}$ Ed., 1995, Mack Publishing Co., Easton, PA, Chapter 83, pp. 1447-1462 (20 pages).

Goodyear et al. (1996), Br J Dermatol. 134(1):85-93, "Immunological studies of herpes simplex virus infection in children with atopic eczema".

Gupta et al. (2007), "Genital herpes", Lancet 370(9605):2127-2137.

Herbert et al. (1995), J Dent 23(6):339-42, "Seroepidemiology of herpes virus infections among dental personnel".

International Search Report for PCT/US2001/062111, dated Apr. 19, 2012 (10 pages).

Kaufman and Faro (1985), Clin. Obstet. Gynecol. 28(1):152-163, "Herpes Genitalis: Clinical Features and Treatment".

Kern et al., "Failure of 2-Deoxy-D-Glucose in the Treatment of Experimental Cutaneous and Genital Infections due to Herpes Simplex Virus," Journal of Infectious Diseases, vol. 146, No. 2, (Aug. 1982) pp. 159-166.

(Continued)

*Primary Examiner* — Elli Peselev
(74) *Attorney, Agent, or Firm* — Merchant & Gould, P.C.

(57) ABSTRACT

The disclosure provides antiviral pharmaceutical compositions comprising one or more antiviral compounds and 2-deoxy-D-glucose in the form of lip-balms, creams and ointments. A specific embodiment discloses a lip-balm composition comprising acyclovir and 2-deoxy-D-glucose.

24 Claims, 2 Drawing Sheets

(56) References Cited

OTHER PUBLICATIONS

Kleymann (2004), Antiviral Chem. & Chemother. 15:135-140, "Helicase primase: targeting the Achilles heel of herpes simplex viruses".

Langeland et al. (1998), Int J. STD AIDS 9(2):104-7, "Prevalence of HSV-2 antibodies among STD clinic patients in Tanzania".

Markoulatos et al. (1995), J Clin Lab Anal 9(5):325-33, "A combined indirect ELISA and immunoblotting for the detection of intrathecal herpes simplex virus IgG antibody synthesis in patients with herpes simplex virus encephalitis".

Markoulatos et al. (1997), J Clin Lab Anal. 11(3):146-53, "Clear detection and typing of herpes simplex virus types 1 and 2 by an indirect ELISA assay: comparison with three different combined methods—capture ELISA, restriction enzymes, and polymerase chain reaction".

Parry et al. (1992), J. Invest. Dermatol. 98(6):856-63, "Acyclovir bioavailability in human skin".

Pechere et al. (1998), Dermatology 197(3):278-280, "Treatment of Acyclovir-Resistant Herpetic Ulceration with Topical Foscarnet and Antiviral Sensitivity Analysis".

Remington's Pharmaceutical Sciences, 18$^{th}$ Ed., 1990, Mack Publishing Co., Easton, PA, Chapter 17 (5 pages).

Spruance et al. (2002), Antimicrob. Agents Chemother. 46(7):2238-2243, "Acyclovir Cream for Treatment of Herpes Simplex Labialis: Results of Two Randomized, Double-Blind, Vehicle-Controlled, Multicenter Clinical Trials".

Shannon et al., "Lack of Efficacy of 2-Deoxy-D-Glucose in the Treatment of Experimental Herpes Genitalis in Guinea Pigs," Antimicrobial Agents and Chemotherapy, vol. 21, No. 3, (Mar. 1982) pp. 513-515.

Supplementary European Search Report and Written Opinion mailed Jul. 3, 3015, for corresponding European Patent Application No. 11876044.6.

\* cited by examiner

TOPICAL ANTIVIRAL FORMULATIONS

CROSS-REFERENCES TO RELATED APPLICATIONS

This application is a Continuation Application of U.S. patent application Ser. No. 13/523,471, filed Jun. 14, 2012, which is a Continuation Application of U.S. patent application Ser. No. 12/572,584, filed Oct. 2, 2009, now U.S. Pat. No. 8,236,768, issued Aug. 7, 2012, which claims the benefit of priority to U.S. Provisional Application No. 61/102,729, filed Oct. 3, 2008, each of which is incorporated herein by reference in its entirety.

STATEMENT REGARDING FEDERALLY SPONSORED RESEARCH OR DEVELOPMENT

Not applicable.

BACKGROUND OF THE DISCLOSURE

1. Field of the Disclosure

The disclosure provides novel topical antiviral pharmaceutical compositions comprising an antiviral compound such as acyclovir and 2-deoxy-D-glucose.

2. Description of the Related Art

Herpes simplex virus (HSV) infections are ubiquitous, with approximately 80% of the adult population infected with HSV type 1 and approximately 20% of the adult population also infected with HSV type 2. HSV type 1 is the cause of herpes labialis, also called orofacial herpes, or cold sores, and HSV encephalitis. HSV type 2 is the primary cause of initial and recurrent genital herpes, and neonatal HSV. The typical manifestation of a primary HSV-1 or HSV-2 genital infection is clusters of inflamed papules and vesicles on the outer surface of the genitals resembling cold sores. (Gupta et al., 2007, "Genital herpes" Lancet 370 (9605): 2127-37).

Herpes viruses cycle between periods of active disease presenting as blisters containing infectious virus particles—that last 2-21 days, followed by a remission period, during which the sores disappear. Many HSV infected people experience recurrence within the first year of infection. During recurrence fewer lesions are likely to develop, lesions are less painful, and lesions heal faster, than those occurring during the primary infection. Subsequent outbreaks tend to be periodic or episodic, occurring on average four to five times a year when not using antiviral therapy.

Treatment of initial HSV infection, and reactivated latent HSV infection, typically includes topical application of an antiviral nucleoside composition to lesions at outbreak. Current prescription topical treatments for herpes labialis include Zovirax® cream (5% acyclovir, GlaxoSmithKline/Biovail Pharmaceuticals, Inc.) which is FDA approved for the treatment of recurrent herpes labialis (cold sores) in adults and adolescents (12 years of age and older). Another topical treatment is Denavir® (1% penciclovir, Novartis), which is FDA approved for the treatment of recurrent herpes labialis (cold sores) in adults. These treatments are noted to inhibit viral replication; shorten healing time and duration of symptoms; and are soothing. Acyclovir and penciclovir are antiviral nucleosides. Zovirax® is applied five times a day for four days. Denavir® is applied every two hours during the day for four days.

Zovirax® ointment (5% acyclovir, GlaxoSmithKline/Biovail Pharmaceuticals, Inc.) is approved for topical administration and is indicated in the management of initial genital herpes and in limited non-life-threatening mucocutaneous Herpes simplex virus infections in immunocompromised patients. Side effects include mild pain upon application, pruritis, and rash.

Several patents list acyclovir as an ingredient in topical formulations for the treatment of herpes simplex genitalis and herpes labialis.

Jones and White, U.S. Pat. No. 4,963,555 is listed in the electronic orange book for Zovirax® topical cream, 5% acyclovir. The '555 patent discloses a topical pharmaceutical formulation for use in treating virus infections of the skin or mucosa and containing 9-(2-hydroxyethoxymethyl)guanine, or a salt or ester thereof, which comprises a dispersed oil phase and a continuous aqueous phase containing therein water, at least 30 wt % of a polyhydric alcohol and solublized acyclovir.

Sintov et al., U.S. Pat. No. 5,585,379, disclose antiviral topical pharmaceutical compositions containing acyclovir dispersed in an aqueous gel carrier containing a gelling agent; a water-soluble carboxylic or dicarboxylic acid salt, such as sodium or potassium oleate; and a polyhydroxy compound such as glycerine, propylene glycol and polyethylene glycol.

Kaufman and Faro, 1999, Clin. Obstet. Gynecol., 28 (1): 152-163 provide a review article describing the clinical features of genital herpes virus infection as well as a discussion of some of the epidemiologic features which may be related to the increased frequency with which this disease is being seen and describing treatment of genital herpes infections.

Spruance et al., 2002, Antimicrob. Agents Chemother. 46 (7): 2238-2243, provide a description of a placebo-controlled clinical trial of a 5% acyclovir topical cream for the treatment of herpes labialis wherein the mean duration of episodes was 4.3 days for patients treated with acyclovir cream and 4.8 days for those treated with the vehicle control.

Certain patents list 2-deoxy-D-glucose as an ingredient in topical formulations for the treatment of herpes simplex genitalis and herpes labialis.

Blough, U.S. Pat. No. 4,603,122, issued Jul. 29, 1986, discloses a method of treating herpes virus infection by the administration of 2-deoxy-D-glucose. For example, for herpes labialis, the topical treatment consisted of two to three drops of a 50 mM solution of 2-deoxy-D-glucose in sterile anhydrous glycerol.

Blough, U.S. Pat. No. 4,315,001, issued Feb. 9, 1982 discloses a method of treating herpes simplex virus by the administration of 2-deoxy-D-glucose.

Blough et al., 1979, J. Am. Med. Assoc, 241(26), 2798-280, describe a clinical study of the treatment of genital herpes infections with 2-deoxy-D-glucose.

Patient satisfaction with current remedies, particularly for HSV-1—herpes labialis, has been poor. Unfortunately, topical acyclovir therapy lacks efficacy as compared to oral or parenteral administrations. The drug concentration in the skin after local application is 2-3 times lower than after given orally (Greg et al., 1992, J. Invest. Dermatol. 98:856-63). It is speculated that the lack of efficacy of topical treatments may be related to the poor water-solubility and lipophilicity of acyclovir, resulting in its inadequate skin or mucous membrane partitioning ability. However, it is still considered safer to give the drug locally.

It is possible that viral resistance to acyclovir should be considered in patients who show poor clinical response during therapy. Resistance of HSV can result from qualitative and quantitative changes in the viral TK and/or DNA polymerase; particularly noted in immunocompromised patients. Clearly, there is room for improvement in topical antiviral compositions for the rapid, efficacious treatment of HSV infections.

It is herein disclosed that a novel topical formulation comprising an antiviral compound and 2-deoxy-D-glucose has been found to be effective in the treatment of HSV infection.

SUMMARY

The disclosure provides a topical antiviral pharmaceutical composition comprising one or more antiviral compounds and 2-deoxy-D-glucose. In one embodiment, the antiviral compound is selected from one or more of acyclovir, vidarabine, azidothymidine, ganciclovir, famciclovir, penciclovir, brivudine, cidofovir, trifluridine, and foscarnet; or a pharmaceutically acceptable salt or hydrate thereof. In a specific embodiment, the antiviral compound is acyclovir.

In one embodiment, the topical composition is in a form selected from a lip-balm, stick, cream or ointment. In one specific aspect, the topical composition is in a lip-balm form. In one aspect, the composition further comprises one or more polyethylene glycols. In another aspect, the composition optionally further comprises one or more sweeteners or flavorings. In one aspect, the sweetener is stevioside. In another aspect, the flavoring is spearmint oil.

In one embodiment, the composition comprises from about 3 wt % to about 7 wt % of acyclovir and from about 0.1 wt % to about 5 wt % of 2-deoxy-D-glucose. In one aspect, the composition comprises about 5 wt % acyclovir and about 0.2 wt % 2-deoxy-D-glucose.

The disclosure also provides a method of treating a herpes viral infection of the skin or mucosa of a mammal which comprises applying to the skin or mucosa a topical composition comprising a therapeutically effective amount of an antiviral compound, or a pharmaceutically acceptable salt thereof, and 2-deoxy-D-glucose. In one embodiment, the method of treating comprises applying to the skin or mucosa a composition comprising one or more antiviral compounds selected from the group consisting of acyclovir, vidarabine, azidothymidine, ganciclovir, famciclovir, penciclovir, brivudine, cidofovir, trifluridine, and foscarnet; and 2-deoxy-D-glucose. In a specific embodiment, the method of treating comprises applying to the skin or mucosa a composition comprising acyclovir and 2-deoxy-D-glucose. In one aspect, the method of treating involves topical application of the composition in a form selected from a lip-balm, stick, cream or ointment. In one specific aspect, the topical composition is in a lip-balm form. In one aspect, the method of treating involves topical application of the composition which further comprises one or more polyethylene glycols. In another aspect, the method of treating involves topical application of the composition further comprising one or more sweeteners or flavorings. In one aspect, the sweetener is stevioside. In another aspect, the flavoring is spearmint oil. In one aspect the method is for treatment of latent infection of herpes simplex type 1 infection. In another aspect, the method is for treatment is for latent infection of herpes simplex type 2 infection.

In one aspect, the method of treating involves topical application of the composition which comprises from about 3 wt % to about 7 wt % of acyclovir and from about 0.1 wt % to about 5 wt % of 2-deoxy-D-glucose. In one aspect, the composition comprises about 5 wt % of the acyclovir and about 0.2 wt % of 2-deoxy-D-glucose.

The disclosure further provides a method of reducing the duration of a herpes viral infection outbreak of the skin or mucosa of a mammal which comprises applying to the skin or mucosa a topical composition comprising a therapeutically effective amount of an antiviral compound, or a pharmaceutically acceptable salt thereof, and 2-deoxy-D-glucose. In one aspect the method is for treatment of latent infection of herpes simplex type 1 infection. In another aspect, the method is for treatment is for latent infection of herpes simplex type 2 infection.

In one embodiment, the method of treating comprises applying to the skin or mucosa a composition comprising one or more antiviral compounds selected from the group consisting of acyclovir, vidarabine, azidothymidine, ganciclovir, famciclovir, penciclovir, brivudine, cidofovir, trifluridine, and foscarnet; and 2-deoxy-D-glucose. In a specific embodiment, the method of treating involves topical application of a composition comprising the antiviral compound acyclovir and 2-deoxy-D-glucose.

DETAILED DESCRIPTION

Figure 1:
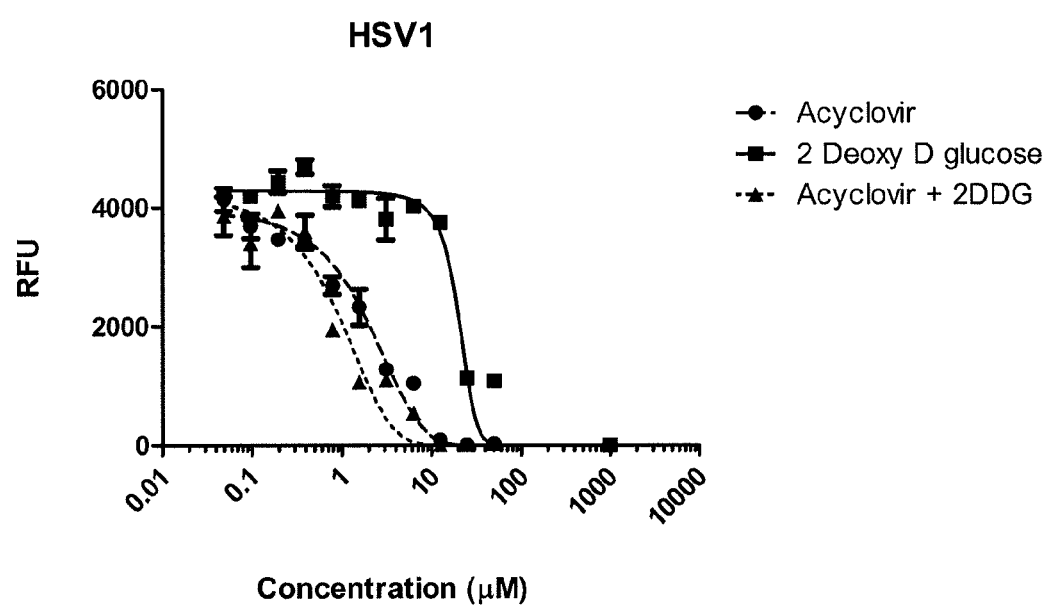
FIG. 1 shows a concentration/response graph for in vitro inhibition of HSV-1 infection of adult human dermal microvascular endothelial cells when treated with acyclovir, 2-deoxy-D-glucose or an equimolar combination of the two compounds.

The disclosure provides a novel topical antiviral pharmaceutical composition comprising one or more antiviral compounds and 2-deoxy-D-glucose. The disclosure provides topical antiviral compositions in the form of a lip-balm, stick, cream, ointment, lotion, gel, plaster, or pen. A specific embodiment discloses a lip-balm stick composition comprising acyclovir and 2-deoxy-D-glucose.

According to one embodiment, the present invention provides a pharmaceutical composition, which comprises a therapeutically effective amount of an antiviral compound, or a pharmaceutically acceptable salt or ester thereof, and 2-deoxy-D-glucose, together with a pharmaceutically acceptable diluent or carrier.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) silica gel; and (22) other non-toxic compatible substances employed in pharmaceutical formulations.

"Optional" or "optionally" means that the subsequently described ingredient may or may not be included in disclosed compositions. "Optionally" is inclusive of embodiments in which the described ingredient is present and embodiments in which the described ingredient is not present.

The use of "wt %" and "w/w" indicates the relative weight percent of a specified ingredient when compared to the weight of the total formulation, unless otherwise specified.

Also included in the family of compounds of the present invention are the pharmaceutically acceptable salts, and esters thereof. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention can be prepared from inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds of by reacting, for example, the appropriate acid or base with the compounds of the present invention.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions. In certain specific embodiments, transdermal, topical formulations are disclosed.

The term "inhibit" or "inhibiting" refers to a statistically significant and measurable reduction in activity, preferably a reduction of at least about 10% versus control, more preferably a reduction of about 20% or more, still more preferably a reduction of about 30% or more.

A "therapeutically effective amount" is an amount of a compound of the present invention or a combination of two or more such compounds, such as an antiviral compound and 2-deoxy-D-glucose, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art. For example, in reference to the treatment of a latent herpes viral infection using the compositions of the present invention, a therapeutically effective amount refers to that amount of an antiviral compound which has the effect of (1) reducing the pain, tingling, burning or itching of the outbreak, (2) reducing the duration of the outbreak, (3) reducing the recurrence of outbreaks, and/or, (4) relieving to some extent (or, preferably, eliminating) one or more other symptoms associated with the outbreak such as, for example, ulceration, crusting, weeping and scabbing.

The term "subject", or "patient", refers to an animal, for example a mammal, who is the object of treatment. Preferably, the patient is a human. The subject, or patient, may be either male or female.

The term "about" when used to refer to a therapeutically effective amount of an antiviral compound, or another compound, includes the specified amount ±10%.

HSV-1 and 2 are virtually identical, sharing approximately 50% of their DNA and having over 80% of common antigens. Both types infect the body's mucosal surfaces, usually the mouth or genitals, and then establish latency in the nervous system. For both types, at least two-thirds of infected people have no symptoms, or symptoms too mild to notice. However, both types can recur and spread even when no symptoms are present. By the time they are teenagers or young adults, about 50% of Americans have HSV-1 antibodies in their blood. By the time they are over age 50, some 80-90% of Americans has HSV-1 antibodies. By comparison, almost all HSV-2 is encountered after childhood, when people become sexually active.

HSVs tend to infect cells of ectodermal origin. After direct exposure to infectious material (i.e., saliva, genital secretions), initial viral replication occurs at the entry site in the skin or mucous membrane. After the initial nonspecific inflammatory response to primary infection, specific antibody response occurs in a few days, followed by a cellular immune response in the second or third week. In persons with cellular immune defects, primary HSV infection can result in life-threatening disseminated disease. In rare cases, the initial replication may lead to disease and life-threatening infection (e.g., encephalitis). After retrograde axonal flow from neurons at the viral point of entry and local replication, the viral genome becomes latent.

HSV latency is defined as the ability to remain in a non-replicating form in the dorsal root ganglia of the CNS. No viral particles are produced during latency. A stimulus (e.g., physical or emotional stress, fever, ultraviolet light) reactivates the virus in the form of skin vesicles or mucosal ulcers, with symptoms less severe than those of the primary infection. Latent HSV can be reactivated from the trigeminal, sacral, and vagal ganglia. Herpes labialis is the most frequent clinical sign of reactivation of HSV infection.

Herpes labialis, also called orofacial herpes, or cold sores, is most often caused by Herpes Simplex Virus Type 1 (HSV-1). Reactivation of HSV, predominantly HSV-1, is rarely associated with systemic signs and symptoms; rather a prodrome of localized pain, tingling (parasthesia), burning, or itching frequently precede recurrent orolabial lesions.

Herpes labialis outbreak proceeds through several stages. Outbreaks can be triggered by any one of several factors including stress, sunlight, fatigue, fever, illness, poor diet, food allergy, and hormonal changes. The prodrome stage may last from a few hours to a few days and is generally accompanied by a tingling or burning sensation around the lips or nose. The blister stage occurs within a day or two of the prodrome stage, there is the first visible sign of clusters of small blisters. The blister stage is followed by the weeping/ulcer stage. This stage is characterized by rupture of the blisters leaving a shallow reddish ulceration. This is the most painful and contagious stage. Viral shedding occurs generally during the first 4-5 days of outbreak commencing during the prodrome stage. The weeping ulcer stage is followed by the crusting stage. A scab with a brown crust forms. If the scab cracks, the sufferer will experience itching, burning and bleeding. The healing stage follows the crusting stage. If a scab has formed, it will flake off during the healing stage.

In recurrent orolabial herpetic infection, the lesions tend to recur at the same site as the original lesions. Pain is most severe at the onset of infection and diminishes after 4-5 days. Patients with primary immunodeficiencies, AIDS, malignancy, malnutrition, or burns and transplant recipients (e.g., bone marrow, organs) receiving immunosuppressive therapy can have unusually severe HSV infections. Beginning antiviral treatment when prodrome is experienced can reduce the appearance and duration of lesions in some individuals.

Genital herpes (herpes genitalis) is a sexually transmitted disease (STD) caused by the herpes simplex viruses type 1 (HSV-1) or type 2 (HSV-2). Most genital herpes is caused by HSV-2. Most individuals have no or only minimal signs or symptoms from HSV-1 or HSV-2 infection. When signs do occur, they typically appear as one or more blisters on or around the genitals or rectum. The blisters break, leaving tender ulcers (sores) that may take two to four weeks to heal the first time they occur. Typically, another outbreak can appear weeks or months after the first, but it almost always is less severe and shorter than the first outbreak. Although the infection can stay in the body indefinitely, the number of outbreaks tends to decrease over a period of years. As in herpes labialis, beginning antiviral treatment when prodrome is experienced can reduce the appearance and duration of lesions.

The disclosure provides topical antiviral compositions which reduce both the severity of symptoms and the duration of HSV infection outbreak. The novel antiviral compositions comprise one or more antiviral compounds and 2-deoxy-D-glucose for the treatment of HSV type 1 and HSV type 2 infections. In one aspect, the disclosure provides a method for reducing reactivation of a latent infection of herpes viruses in a human comprising topically administering a pharmaceutical composition comprising a therapeutically effective amount of an antiviral compound and 2-deoxy-D-glucose.

Antiviral compounds to be combined with 2-deoxy-D-glucose in the compositions of the present disclosure are selected from one or more of, but are not limited to, certain antiviral nucleosides including Acyclovir (9-(2-hydroxy-ethoxymethyl)guanine; 2-Amino-1,9-dihydro-9-((2-hydroxyethoxy)methyl)-6H-purin-6-one; CAS No. 59277-89-3; M.W. 225.207 g/mol), Acyclovir sodium (2-Amino-1,9-dihydro-9((2-hydroxyethoxy)methyl)-6H-purin-6-one monosodium salt, CAS No. 69657-51-8; M.W. 247.189 g/mol), Vidarabine (adenine arabinoside; CAS No. 5536-17-4), Vidarabine monohydrate (9-beta-D-Arabinofuranosyl-9H-purine-6-amine monohydrate; CAS No. 24356-66-9); Azidothymidine (AZT, Retrovir, Zidovudine, 3-azido-3"-deoxythymidine; CAS No. 30516-87-1), Ganciclovir (9-(1, 3-dihydroxy-2-propoxy)methylguanine, DHPG; CAS No. 82410-32-0), Ganciclovir sodium (9-((2-Hydroxy-1-(hydroxymethyl)ethoxy)methyl)guanine, Sodium; 2-amino-1,9-dihydro-9-((2-hydroxy-1-(hydroxymethyl)ethoxy)methyl)-6H-purin-6-one monosodium salt; CAS No. 107910-75-8 or 84245-13-6); Famciclovir (1,3-Propanediol, 2-(2-(2-amino-9H-purin-9-yl)ethyl)-, diacetate (ester); CAS No. 104227-87-4), Penciclovir (9-(4-Hydroxy-3-(hydroxymethyl)butyl) guanine; CAS No. 39809-25-1), Brivudine ((E)-5-(2-Bromovinyl)-2'-deoxyuridine; CAS No. 69304-47-8); Cidofovir (Phosphonic acid, ((2-(4-amino-2-oxo-1(2H)-pyrimidinyl)-1-(hydroxymethyl)ethoxy)methyl)-, (S)—; CAS No. 113852-37-2); Trifluridine (5-Trifluorothymidine; CAS No. 70-00-8) and any salts or hydrates thereof. The antiviral nucleosides may be obtained commercially, or produced by synthetic procedures known in the art, for example, as described in Izawa and Shiragami, 1998, "Practical syntheses of antiviral nucleosides", Pure & Appl. Chem., 70(2): 313-318.

In one embodiment, the topical antiviral compositions contain from about a total of about 0.1 to about 10 wt % of one or more antiviral compounds and 2-deoxy-D-glucose. In one aspect, the topical antiviral composition comprises from about 3 wt % to about 7 wt % of an antiviral compound. In another aspect, the topical antiviral compound is present from about 0.5 wt % to about 4 wt % of an antiviral compound. In yet another embodiment, the topical antiviral compound is present in from about 1% to about 3% weight compared to the total weight of the formulation.

Acyclovir is a synthetic purine nucleoside analogue with in vitro and in vivo inhibitory activity against herpes simplex virus types 1 (HSV-1), 2 (HSV-2), and varicella-zoster virus (VZV). The inhibitory activity of acyclovir is highly selective due to its affinity for the enzyme thymidine kinase (TK) encoded by HSV and VZV. This viral enzyme converts acyclovir into acyclovir monophosphate, a nucleotide analogue. The monophosphate is further converted into diphosphate by cellular guanylate kinase and into triphosphate by a number of cellular enzymes. In vitro, acyclovir triphosphate stops replication of herpes viral DNA. This is accomplished in 3 ways: 1) competitive inhibition of viral DNA polymerase, 2) incorporation into and termination of the growing viral DNA chain, and 3) inactivation of the viral DNA polymerase. The greater antiviral activity of acyclovir against HSV compared to VZV is due to its more efficient phosphorylation by the viral TK.

It is noted in the Zovirax® (acyclovir) Cream 5% prescribing information that resistance of HSV to acyclovir can result from quantitative and qualitative changes in the viral TK and/or DNA polymerase. Clinical isolates of HSV with reduced susceptibility to acyclovir have been recovered from immunocompromised patients, especially with advanced HIV infection. Most of the acyclovir-resistant mutants isolated thus far from immunocompromised patients have been TK-deficient mutants, other mutants involving the viral TK-gene (TK partial and TK altered) and DNA polymerase have been isolated. TK-negative mutants cause severe disease in immunocompromised patients and infants. The possibility of viral resistance to acyclovir should be considered in patients who show poor clinical response during therapy. A multi-therapeutic approach to topical antiviral compositions is herein disclosed as one solution to the problem of resistance. The disclosure provides compositions comprising one or more antiviral compounds and 2-deoxy-D-glucose.

The antiviral action of 2-deoxy-D-glucose has been known for decades. 2-deoxy-D-glucose (deoxyglucose; 2-deoxy-D-arabino-hexose; 2-deoxy-D-mannose; 2-desoxy-D-glucose; CAS No. 154-17-6; M.W. 164.156 g/mol) is incorporated directly into glycoproteins and glycolipids and appears to block the cellular synthesis of the major glycosylated polypeptide of the herpes virus. For example, in HSV-infected cells treated with 2-deoxy-D-glucose, hematosides are notably reduced, with an accumulation of precursor molecules, namely, the ceramide backbone. In addition, 2-deoxy-D-glucose appears to prevent the synthesis and transport of nonstructural glycolipids. 2-Deoxy-D-glucose, therefore, is a rational and effective chemotherapetic agent in the treatment of genital herpes because of its ability to prevent the synthesis of macromolecules required for the envelope biogenesis and recognition phenomenon. 2-deoxy-D-glucose may be purchased commercially. In one embodiment, the topical antiviral compositions contain from about 0.1 to about 10 wt % of 2-deoxy-D-glucose. In one aspect, the topical antiviral composition comprises from about 0.1% to about 5% of 2-deoxy-D-glucose.

The compositions of the disclosure contain a weight ratio of antiviral compound to 2-deoxy-D-glucose from about 1:100 to about 100:1. In one embodiment, the weight ratio of antiviral compound to 2-deoxy-D-glucose is from about 1:30 to about 30:1. In a specific aspect, the ratio of acyclovir to 2-deoxy-D-glucose is about 25:1. In one specific aspect, the molar ratio of acyclovir to 2-deoxy-D-glucose is about 18:1. In another specific aspect, the molar ratio of acyclovir to 2-deoxy-D-glucose is about 1:1.

In a specific embodiment, the antiviral compound is acyclovir. In a specific aspect, the topical antiviral composition comprises from about 3 wt % to about 7 wt % acyclovir. In a preferred specific aspect, the topical antiviral composition comprises from about 5 wt % acyclovir. In another specific aspect, the topical antiviral composition comprises from about 0.1 wt % to about 5 wt % of 2-deoxy-D-glucose.

In another embodiment, the disclosure provides a formulation comprising penciclovir and 2-deoxy-D-glucose. Penciclovir is an acyclic nucleoside analog available as a 1% topical cream for the treatment of recurrent herpes labialis (cold sores) in adults (Denavir®, Novartis). In one aspect, the penciclovir is present in from about 0.1% to about 5 wt % of the weight of the formulation. In a specific aspect, the penciclovir is present in about 1 wt % of the total weight of the formulation. In another specific aspect, the topical antiviral composition comprises from about 0.1% to about 5 wt % of 2-deoxy-D-glucose.

In another embodiment, the disclosure provides a topical formulation comprising the non-nucleoside antiviral compound foscarnet and 2-deoxy-D-glucose. Foscarnet is a phosphonic acid derivative marketed as foscarnet sodium in an injectable formulation (Foscavir®, AstraZeneca). Foscarnet is an antiviral medication used to treat herpes viruses, including drug resistant cytomegalovirus (CMV) and herpes simplex viruses types 1 and 2 (HSV-1 and HSV-2). Topical foscarnet has been used to treat severe genital ulceration due to acyclovir-resistant HSV-2. See Pechere et al., Dermatology, 1998; 197:278-280. In one aspect, the foscarnet is present in from about 1 wt % to about 5 wt % of the total weight of the formulation. In a specific aspect, foscarnet is present in about 2.4 wt % of the weight of the formulation. In another specific aspect, the topical antiviral composition comprises from about 0.1% to about 5 wt % of 2-deoxy-D-glucose.

In one embodiment, the topical antiviral composition can optionally further comprise one or more sweeteners. The optional sweetener is added to increase patient acceptability and compliance with the recommended dosing schedule. However, the sweetener may not be selected from a simple sugar, as the presence of the simple sugar may interfere with the action of the 2-deoxy-D-glucose. The sweetener may be selected from a synthetic or natural sweetener, for example, aspartame, a cyclamate, saccharin, acesulfame salts, neohesperidin dihydrochalcone, sucralose, alitame, astevia, stevioside, talin, glycerrhizin, thaumatin, xylitol, and mixtures thereof. The term saccharin as used herein includes saccharin itself, saccharin acids, and saccharin salts such as sodium saccharin. In one aspect, the sweetener is stevioside. The sweetener is optionally present from about 0.1% to about 5 wt % of the weight of the topical antiviral compositions.

In another embodiment, the topical antiviral composition can optionally further comprise one or more flavoring agents. The optional flavoring agent is added to increase patient acceptability and compliance with the recommended dosing schedule. The flavoring agents that may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. In a specific aspect, the flavoring is spearmint oil. The flavor is optionally present from about 0.1% to about 5% by weight of the topical antiviral composition.

In a further embodiment, the topical antiviral composition can optionally further comprise one or more colorants and/or opacifiers in order to blend with the skin tone of the patient, so long as the colorant or opacifier does not interfere with the antiviral action of the formulation. Colorants include such compounds as, by way of example and without limitation, titanium dioxide, talc, FD&C Red No. 3, FD&C Red No. 20, FD&C Yellow No. 6, FD&C Blue No. 2, FD&C Green No. 5, FD&C Orange No. 5, FD&C Red No. 8, caramel, ferric oxide, other FD&C dyes, lakes, and natural coloring agents such as grape skin extract, beet red powder, beta-carotene, annato, carmine, turmeric, paprika, and other materials known in the art. The amount of coloring agent used will vary as desired.

The topical composition carrier formulation should be stable and pharmaceutically acceptable. The composition should also enable incorporation of sufficient amounts of the active ingredients to give the proper penetration characteristics. In addition to conventional excipient ingredients in lipbalms, sticks, creams, lotions, gels or ointments, compositions based on phospholipids, including sphingolipids can be advantageous. Various absorbent ointment bases, emulsion ointment bases and water soluble ointment bases and components are known in the art and may be utilized in the compositions of the present disclosure, for example, as described in Remington's Pharmaceutical Sciences, Eighteenth Ed. 1990, Mack Publishing Co., Easton Pa., pp. 1311-1314. Ointment carrier bases may include, but are not limited to, waxes, petrolatum, esters of fatty alcohols, and saturated fatty acids, oleic acid, olive oil, paraffin, starch glycerin, lanolin, cetyl alcohol, glyceryl monostearate, methylparaben, propylparaben, glycol ethers, polyethylene glycols, polyoxyl 40 stearate, and polysorbates. The composition may further comprise optional additional ingredients selected from one or more of a penetration enhancer, oil, waxy compound, surfactant, stabilizer, gelling agent, moisturizer, water or a preservative.

Optional penetration enhancers serve to improve the absorption across the skin of the antiviral compound. Penetration enhancers include vitamin E TPGS (Eastman Chemical Company, Kingsport, Tenn.), and other vitamin E derivatives as described in U.S. Pat. No. 6,193,985, which is incorporated herein by reference; and glyceryl monocaprylate/caprate (Cornwell et al. 1998, Int. J. Pharmaceutics, 171 (2): 243-255). Other penetration enhancers are described in Smith and Maibach (eds.), *Percutaneous Penetration Enhancers*, CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997).

The oils, waxy compounds, gelling agents and surfactants selected for the formulation and stabilization of these compositions are those traditionally employed in the dermatological arts. The optional oils and/or waxy compounds can constitute from 0.5% to 99.9% of the total weight of the composition. The amount of oil and/or wax depends on the actual form or physical state of the composition. Exemplary of such oils are mineral oils (petrolatum); vegetable oils (sweet almond, macadamia, blackcurrant-pip oil); synthetic oils such as perhydrosqualene, fatty alcohols, acids or esters (octyl palmitate, isopropyl lanolate, triglycerides including those of capric/caprylic acids), oxyethylenated or oxypropylenated fatty esters and ethers; and silicone oils (cyclomethicone, polydimethylsiloxanes or PDMS) or fluorinated oils. Exemplary waxy compounds include jojoba oil, paraffin, carnauba wax and beeswax.

Exemplary surfactants (emulsifying and coemulsifying) include the esters of fatty acids and polyethylene glycol (PEG), esters of fatty acids and glycerol (glyceryl stearate) or esters of fatty acids and sugar (sorbitan stearate), as well as the polyoxyethylenated or polyoxypropylenated derivatives thereof, cyclomethicones and dimethicone copolyols, and also anionic surfactants (K or Na alkyl phosphate).

A preferred stabilizer includes glycol stearate or PEG-150 distearate. The stabilizer, when used, is typically present in an amount from about 0.1 to 5 weight percent of the composition.

Exemplary gelling agents include modified clays (bentones), metal salts of fatty acids (aluminum stearate), ethylene/acrylate copolymers, silicas, polyethylenes, calcium silicates or, alternatively, ethyl cellulose.

Preferred moisturizers include wheat protein (e.g., laurdimonium hydroxypropyl hydrolyzed wheat protein), hair keratin amino acids, sodium peroxylinecarbolic acid, panthenol, tocopherol (Vitamin E), dimethicone, and the like, and mixtures thereof. Sodium chloride may also be present, particularly when hair keratin amino acids are included as a moisturizer. Moisturizers, when used, are typically present in an amount from about 0.01 to 2 weight percent, preferably about 0.05 to 1.5 weight percent, more preferably from about 0.1 to 1 weight percent of the composition.

The water used is preferably deionized water.

Preferred preservatives include tetrasodium ethylene-diamine tetraacetic acid (EDTA), methylparaben, benzophenone-4, methylchloroisothiazolinone, methylisothiazolinone, and the like, and mixtures thereof. Preservatives, when used, are typically present in an amount from about 0.01 to 6 weight percent, preferably about 0.05 to 4 weight percent, and more preferably from about 0.1 to 2 weight percent.

In one embodiment, the disclosure provides a composition comprising one or more antiviral compounds and 2-deoxy-D-glucose in a lip-balm stick carrier formulation. In one aspect, the lip balm stick carrier formulation is comprised of one or more polyethylene glycols (PEGs). In a specific aspect, the lip-balm stick carrier formulation is comprised of PEG 1450, PEG 300, silica gel, a flavoring and a sweetener. The final mixture described above is poured, while still warm and fluid, into appropriate tubes and allowed to cool until solid. The resulting lip balm of the present disclosure is in the form of a stick. However, the lip balm of the present disclosure can also be marketed in a small wide mouth jar. One preferred specific embodiment is shown in Example 4.

In another embodiment, the disclosure provides a composition comprising acyclovir and 2-deoxy-D-glucose in an aqueous cream carrier formulation. Preparation of aqueous creams is described, for example, in U.S. Pat. No. 4,963,555, expired, which is incorporated herein by reference. In one aspect, the aqueous cream comprises 5 wt % acyclovir and 0.2 wt % 2-deoxy-D-glucose. A specific embodiment is shown in Example 5.

In another embodiment, the disclosure provides a composition comprising acyclovir and 2-deoxy-D-glucose in an ointment carrier formulation. In one aspect the ointment carrier formulation comprises a polyethylene glycol.

In one embodiment, the disclosure provides a method of treating an HSV infection outbreak by topically administering a composition comprising an antiviral compound and 2-deoxy-D-glucose. A composition of the present disclosure can be administered topically to the affected area in a single daily dose or in multiple doses per day. In one aspect, the composition is administered four times a day. In another aspect, the composition is administered every three hours during waking hours. In another aspect, the composition is topically administered every two hours during waking hours. The treatment regimen may require administration from a single dose up to multiple daily doses for an extended period of time, for example, for several days or from one to two weeks. In one specific aspect, the treatment regimen is topical application of the composition every 2 hours during waking hours for 5 days. The amount of antiviral compound and 2-deoxy-D-glucose administered per dose or the total amount administered will depend on such factors as the nature and severity of the infection, the age and general health of the patient.

In one aspect, an equimolar combination of the two compounds acyclovir and 2-deoxy-D-glucose is unexpectedly more effective than either individual compound at inhibiting HSV infection of primary Adult Human Dermal Microvascular Endothelial Cells in vitro. In vitro assays for anti-HSV-1 and anti-HSV-2 mRNA activity are described in Example 1. Confluent Vero cell monolayers were infected with HSV type 1 or HSV type 2 at a multiplicity of infection of 10 and the resultant virus was used to infect primary Adult Human Dermal Microvascular Endothelial Cells for 1 hour; the supernatant was replaced with fresh culture media and then incubated overnight in the presence of various concentrations of acyclovir, 2-deoxy-D-glucose or an equimolar combination of the two compounds. After overnight incubation, the cells were harvested, lysed, and subjected to QuantiGene Plex 2.0 assay (Panomics, Inc., Fremont, Calif.) for quantitative assay of HSV-1 and HSV-2 mRNA. The QuantiGene Plex 2.0 assay combines branched DNA (bDNA) signal amplification and multi-analyte profiling beads (xMAP®) technologies to enable the detection and quantitation of multiple mRNA targets simultaneously.

Figure 2:
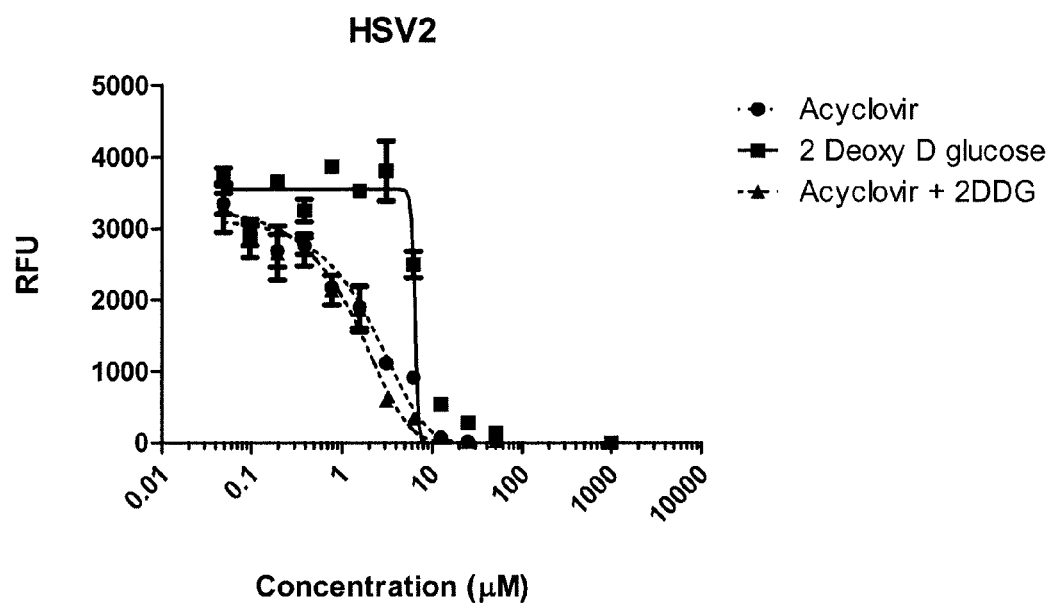
FIG. 2 shows a concentration/response graph for in vitro inhibition of HSV-2 infection of adult human dermal microvascular endothelial cells when treated with acyclovir, 2-deoxy-D-glucose or an equimolar combination of the two compounds.

FIGS. 1 and 2 show concentration/response graphs for inhibition of HSV-1 and HSV-2 infection of human endothelial cells when treated with various concentrations of acyclovir, 2-deoxy-D-glucose or an equimolar combination of the two compounds. Particularly, FIG. 1 shows a statistically significant leftward shift of the dose-response curve for the combination of acyclovir and 2-deoxy-D-glucose ($IC_{50}$=1.009 µM) as compared to either acyclovir ($IC_{50}$=1.782 µM) or 2-deoxy-2-D-glucose ($IC_{50}$=20.9 µM). Thus, the combination of acyclovir and 2-deoxy-D-glucose is unexpectedly more effective than either individual compound at inhibiting HSV infection in vitro. The combination of acyclovir and 2-deoxy-D-glucose can also be tested in vitro in either HSV-1 or HSV-2 IgG ELISAs, as described in Examples 2 and 3.

In one embodiment, the disclosure provides a method of treating an HSV infection outbreak by application of the composition of the present disclosure to a patient in need thereof. In one aspect, the disclosure provides a method of decreasing the duration of an outbreak of herpes labialis by application of the composition of the present disclosure to a patient in need thereof. In another aspect, application of the composition of the present disclosure reduces the recurrence of outbreaks of herpes labialis in a patient in need thereof. In one aspect, the compositions of the present disclosure reduce the severity of outbreaks of herpes labialis in clinical patients. In another aspect, the compositions of the present disclosure reduce the pain associated with outbreaks of herpes labialis in clinical patients.

In a preliminary, non-placebo controlled clinical trial, patients diagnosed with herpes labialis were referred from a dentist with a prescription for acyclovir. Patients either had an ongoing outbreak, or were known to be susceptible to recurrent outbreak following dental work. Patients received the lip-balm formulation of Example 4 as described in Example 6. Patient surveys were collected. Data is presented in Table 5. A reduction in the duration of the outbreak from an average of 10.8 days to 5.2 days was seen in patients who were administered the formulation of Example 4. The frequency in the number of annual outbreaks was reduced from 6.2 to 1.9 per year. Generally, if treatment was started early at prodrome, no visual outbreak would occur. A reduction in duration and severity of symptoms was seen if treatment was started at blister or early crust. Occasionally, outbreak persisted if treatment was started after prodrome, but an improvement in symptoms occurred including relief of stinging and/or reduction in visual severity. The formulation was considered pleasant.

EXAMPLES

Example 1

In Vitro Assay for Anti-HSV-1 and Anti-HSV-2 mRNA Activity

Briefly, confluent Vero cell monolayers were infected with HSV type 1 or HSV type 2 at a multiplicity of infection of 10 and the resultant virus was used to infect primary Adult Human Dermal Microvascular Endothelial Cells for 1 hour and then the supernatant was replaced with fresh culture media and then incubated overnight in the presence of various concentrations of acyclovir, 2-deoxy-D-glucose or an equimolar combination of the two compounds. After overnight incubation, the cells were harvested, lysed, and subjected to QuantiGene Plex 2.0 assay (Panomics, Inc., Fremont, Calif.) for quantitative assay of HSV-1 and HSV-2 mRNA. The QuantiGene Plex 2.0 assay combines branched DNA (bDNA) signal amplification and multi-analyte profiling beads (xMAP®) technologies to enable the detection and quantitation of multiple mRNA targets simultaneously. Generally, this assay is considered to be a more sensitive and specific assay (bDNA) for the final readout when compared to an ELISA. The ELISA method while easier, can lack specificity to determine the difference between HSV1 and HSV2.

The bDNA assay is a hybridization-based method of target-specific RNA quantitation that amplifies signal rather than target RNA, using labeled DNA probes. The QuantiGene Plex 2.0 system utilizes fluorescent microspheres (Capture Beads) as a support to capture specific RNA molecules. The ability to quantify multiple target-specific RNA molecules in a single sample lies in the design of the Probe Sets. For each RNA molecule of interest, an oligonucleotide Probe Set containing three types of synthetic probes, Capture Extenders (CEs), Label Extenders (LEs), and Blockers (BLs) that hybridize and span contiguous sequences of the target RNA, is provided. The CEs discriminate among the different Capture Beads within the bead array while capturing, via cooperative hybridization, the target RNA.

Signal amplification is mediated by DNA amplification molecules that hybridize to the tails of the LEs. Each amplification unit contains multiple hybridization sites for biotinylated Label Probes that bind Streptavidin-conjugated R-Phycoerythrin (SAPE). The resulting fluorescence signal associated with individual Capture Beads is read on a Luminex flow cytometer. Signal is reported as median fluorescence intensity (MFI) and is proportional to the number of target RNA molecules present in the sample. All compounds were run in triplicate for each concentration. Concentrations are expressed in micromolar (µM) concentrations.

The $IC_{50}$ (the drug concentration that reduces the number of virally infected cells by 50%) were determined by plotting the reduction in fluorescence (RLU) versus the drug concentration using Graph Pad Prism software. Specifically, the variable slope model was used to calculate the $IC_{50}$s with the formula "Y=Bottom+(Top-Bottom)/(1+10^((Log IC50-X)*HillSlope))" using Graph Pad Prism software. The data is shown graphically in FIGS. 1 and 2. The error bars represent the standard error of the mean (SEM). The statistics for each evaluation are shown in Tables 1 and 2.

TABLE 1

$IC_{50}$ of Acyclovir and/or 2-Deoxy-D-glucose against HSV-1.

| Nonlin fit of HSV1 | Acyclovir | 2 Deoxy D glucose | Acyclovir + 2DDG |
|---|---|---|---|
| log(inhibitor) response -- vs. Variable slope Best-fit values | | | |
| LogIC50 | 0.2509 | 1.32 | 0.003803 |
| HillSlope | −1.108 | −2.395 | −1.406 |
| IC50 | 1.782 | 20.9 | 1.009 |

TABLE 1-continued $IC_{50}$ of Acyclovir and/or 2-Deoxy-D-glucose against HSV-1.

| Nonlin fit of HSV1 | Acyclovir | 2 Deoxy D glucose | Acyclovir + 2DDG |
|---|---|---|---|
| Std. Error | | | |
| LogIC50 | 0.05128 | 0.03338 | 0.06276 |
| HillSlope | 0.1179 | 0.3951 | 0.2286 |
| 95% Confidence Intervals | | | |
| LogIC50 | 0.1463 to 0.3555 | 1.252 to 1.388 | −0.1240 to 0.1316 |
| HillSlope | −1.349 to −0.8678 | −3.200 to −1.590 | −1.871 to −0.9403 |
| IC50 | 1.401 to 2.267 | 17.87 to 24.45 | 0.7517 to 1.354 |
| Goodness of Fit | | | |
| Degrees of Freedom | 31 | 32 | 33 |
| $R^2$ | 0.9715 | 0.9377 | 0.9422 |
| Number of points | | | |
| Analyzed | 34 | 35 | 36 |

TABLE 2

$IC_{50}$ of Acyclovir and/or 2-Deoxy-D-glucose against HSV-2.

| Nonlin fit of HSV2 | Acyclovir | 2 Deoxy D glucose | Acyclovir + 2DDG |
|---|---|---|---|
| log(inhibitor) response vs. -- Variable slope Best-fit values | | | |
| LogIC50 | 0.2805 | 0.9029 | 0.212 |
| HillSlope | −1.113 | −3.957 | −1.543 |
| IC50 | 1.908 | 7.996 | 1.629 |
| Std. Error | | | |
| LogIC50 | 0.05897 | 0.03075 | 0.05944 |
| HillSlope | 0.1338 | 0.8319 | 0.2717 |
| 95% Confidence Intervals | | | |
| LogIC50 | 0.1605 to 0.4005 | 0.8402 to 0.9655 | 0.09102 to 0.3330 |
| HillSlope | −1.386 to −0.8410 | −5.652 to −2.262 | −2.096 to −0.9895 |
| IC50 | 1.447 to 2.515 | 6.922 to 9.237 | 1.233 to 2.153 |
| Goodness of Fit | | | |
| Degrees of Freedom | 33 | 32 | 33 |
| $R^2$ | 0.9618 | 0.945 | 0.9366 |
| Number of points | | | |
| Analyzed | 36 | 35 | 36 |

In these assays, the combination of the two compounds acyclovir and 2-deoxy-D-glucose was unexpectedly more effective at inhibiting HSV infection of cells in vitro than either compound individually, as shown by a comparison of the IC50 as well as the concentration/response graphs shown in FIGS. 1 and 2. Particularly, FIG. 1 shows a statistically significant leftward shift of the dose-response curve for the combination of acyclovir and 2-deoxy-D-glucose ($IC_{50}$=1.009 µM) as compared to either acyclovir ($IC_{50}$=1.782 µM) or 2-deoxy-2-D-glucose ($IC_{50}$=20.9 µM).

Example 2

HSV-1 IgG ELISA

The presence of HSV IgG antibody is indicative of previous exposure. A significant increase in HSV IgG is indicative of reactivation, current or recent infection. IgM antibody is present after primary HSV infection. The CALBIOTECH INC. (CBI, Spring Valley, Calif., Cat. No. H1029G or H1029G4) HSV-1 ELISA Test system can be used to test for the presence of HSV-1 IgG. A biological sample is subjected to the HSV-1 ELISA which is an enzyme-linked immunosorbant assay for the detection of IgG class antibodies to HSV-1 in human serum. Generally, the CBI HSV-1 IgG ELISA package insert directions are followed. HSV-1 antigen coated wells are provided, along with positive and negative controls and calibrators. For example, diluted patient serum is added to wells coated with purified antigen. IgG specific antibody, if present, binds to the antigen. All unbound materials are washed away and the enzyme conjugate is added to bind to the antibody-antigen complex, if present. Excess enzyme conjugate is washed off and TMB substrate is added. The plate is incubated at room temperature for 10 minutes to allow the hydrolysis of the substrate by the enzyme. Stop solution is added after 10 minutes. The ELISA plate O.D. is read at 450 nm. The intensity of the color generated is proportional to the amount of IgG specific antibody in the sample. Generally, an antibody index <0.9 is interpreted as no detectable antibody to HSV-1 IgG by ELISA; an antibody index of 0.9-1.1 is a borderline positive; and an antibody index >1.1 indicates detectable antibody to HSV-1 IgG by ELISA.

Example 3

HSV-2 IgG ELISA

The presence of HSV IgG antibody is indicative of previous exposure. A significant increase in HSV IgG is indicative of reactivation, current or recent infection. IgM antibody is present after primary HSV infection. The CALBIOTECH INC. (CBI, Spring Valley, Calif., Cat. No. H2031G or H2031 G4) HSV-2 ELISA Test system can be used to test for the presence of HSV-2 IgG. A biological sample is subjected to the HSV-2 ELISA which is an enzyme-linked immunosorbant assay for the detection of IgG class antibodies to HSV-2 in human serum or plasma.

Generally, the CBI HSV-2 IgG ELISA package insert directions are followed. HSV-2 antigen coated wells are provided, along with positive and negative controls and calibrators. For example, diluted patient serum is added to wells coated with purified antigen. IgG specific antibody, if present, binds to the antigen. All unbound materials are washed away and the enzyme conjugate is added to bind to the antibody-antigen complex, if present. Excess enzyme conjugate is washed off and TMB substrate is added. The plate is incubated at room temperature for 10 minutes to allow the hydrolysis of the substrate by the enzyme. Stop solution is added after 10 minutes. The ELISA plate O.D. is read at 450 nm. The intensity of the color generated is proportional to the amount of IgG specific antibody in the sample. Generally, an antibody index <0.9 is interpreted as no detectable antibody to HSV-2 IgG by ELISA; an antibody index of 0.9-1.1 is a borderline positive; and an antibody index >1.1 indicates detectable antibody to HSV-2 IgG by ELISA.

Example 4

Antiviral Topical Formulations. Lip-Balm Formulation

Ingredients for one batch of a lip-balm formulation comprising about 5% w/w of acyclovir and 0.2% w/w 2-deoxy-D-glucose are provided in Table 3.

TABLE 3

Lip-balm Formulation.

| Ingredient | Amount | specific gravity | Amount per chapstick | % (w/w) |
|---|---|---|---|---|
| Acyclovir, USP | 1.6667 g | | 0.333 g | 4.5 |
| 2-Deoxy-D-glucose | 0.0667 g | | 0.0133 g | 0.2 |
| Silica gel, USP/NF powder | 0.200 g | | 0.04 g | 0.5 |
| Stevioside, 90% powder | 0.3333 g | | 0.0667 g | 0.9 |
| Polyethylene glycol 1450, NF granules | 16.25 g | | 3.25 g | 43.6 |
| Polyethylene glycol 300, NF liquid | 16.6667 mL | 1.1 | 3.33 mL | 49.1 |
| Flavor, spearmint oil | 0.5 mL | 0.917 | 0.1 mL | 1.2 |

The polyethylene 1450 and 300 was melted at 50° C. with stirring. The acyclovir, 2-deoxy-D-glucose, silica gel and stevioside were triturated together. The triturated powders were slowly sifted into the melted PEGs with stirring. The flavoring was added, followed by thorough mixing. The mixture was poured into applicator tubes and allowed to cool to room temperature. Amounts of acyclovir and 2-deoxy-D-glucose employed may be varied in accordance with the specification.

Example 5

Antiviral Topical Formulations. Aqueous Cream Formulation

Ingredients for one batch of an aqueous cream formulation comprising about 5% w/w of acyclovir and 0.2% w/w 2-deoxy-D-glucose are provided in Table 4.

TABLE 4

Aqueous Cream Formulation.

| Ingredient | Amount | % (w/w) |
|---|---|---|
| Acyclovir, USP | 50.0 g | 5 |
| 2-Deoxy-D-glucose | 2.0 g | 0.2 |
| Cetostearyl alcohol | 67.5 g | |
| Sodium lauryl sulphate | 7.5 g | |
| White soft paraffin | 125.0 g | |
| Liquid paraffin | 50.0 g | |
| Propylene glycol | 400.0 g | |
| Purified water, Q.S. to | 1000.0 g | |

A part of the acyclovir (5 g) is dissolved in the water with the 2-deoxy-D-glucose and propylene glycol at ambient temperature to produce an aqueous solution. The paraffins and emulsifiers (cetostearyl alcohol and sodium lauryl sulphate) are mixed together and heated to 60° C., and emulsified with the aqueous solution, also at 60° C., using a laboratory mixer. The remaining acyclovir is added, the mixture dispersed, allowed to cool, and filled into lacquered aluminum tubes. Amounts of acyclovir and 2-deoxy-D-glucose employed may be varied in accordance with the specification.

Example 6

Clinical Results

Patients diagnosed with herpes labialis were referred from a dentist with a prescription for acyclovir. Patients had an ongoing outbreak, or were known to be susceptible to recurrent outbreak following dental work. A patient population comprising about 40 patients received the lip-balm formulation of Example 4. Data to verify treatment outcomes, adverse effects and patient comment was collected by patient survey several months after dispensing the formulation. Sixteen patients returned the survey to date. Surveyed patients ranged in age from 14 to 65 years old, with an average age of 42 years old. Nine males and seven females returned the survey. Patients used the formulation for an average of 4.8 days on average every 2-3 hours following outbreak signs of prodrome or early crust. Table 5 shows data collected from patient surveys.

TABLE 5

Clinical Data.

| Patient No. | Age | Gender F | Gender M | Duration of outbreak Days Prior | Duration of outbreak Days During use | Frequency of outbreak Number per year Prior | Frequency of outbreak Number per year During use |
|---|---|---|---|---|---|---|---|
| 1 | 28 | 1 | 0 | 10 | 5 | 12 | 6 |
| 2 | 14 | 0 | 1 | 12 | 6 | 7 | 2.5 |
| 3 | 44 | 1 | 0 | 10.5 | 3 | 6 | 1 |
| 4 | 53 | 1 | 0 | 14 | 7 | 2 | 1 |
| 5 | 65 | 0 | 1 | 7 | 5 | 4.5 | 0 |
| 6 | 38 | 0 | 1 | 14 | 9 | 5 | 3 |
| 7 | 39 | 1 | 0 | 14 | 7 | 2.5 | 1.5 |
| 8 | 62 | 0 | 1 | 4 | 2 | 4 | 0 |
| 9 | 40 | 1 | 0 | 7 | 1.5 | 4 | n/a |
| 10 | 55 | 0 | 1 | 10.5 | 5 | 17 | 1 |
| 11 | 42 | 1 | 0 | 12 | 6 | 6 | n/a |
| 12 | 38 | 0 | 1 | 10 | 6 | 5 | n/a |
| 13 | 17 | 0 | 1 | 12 | 8 | 2.5 | n/a |
| 14 | 48 | 0 | 1 | 11 | 4 | 4.5 | n/a |
| 15 | 45 | 0 | 1 | 12 | 2 | 4.5 | n/a |
| 16 | 45 | 1 | 0 | 12 | 7 | 13 | 3 |
| Average | 42.1 | 7.0 | 9.0 | 10.8 | 5.2 | 6.2 | 1.9 |
| Std. Dev. | 14.0 | | | 2.8 | 2.2 | 4.2 | 1.9 |

A reduction in the duration of the outbreak from an average of 10.8 days to 5.2 days was seen in all patients surveyed. The frequency in the number of annual outbreaks was reduced from 6.2 to 1.9 per year. Generally, if treatment was started early at prodrome, no visual outbreak would occur. A reduction in duration and severity of symptoms was seen if treatment was started at blister or early crust. Occasionally outbreak persisted if treatment was started after prodrome, but an improvement in symptoms occurred; including relief of stinging, reduction in visual severity and/or shortened crusting time. Patient acceptability was good with comments on pleasant smell.

Example 7

Further Clinical Results

As in Example 5, patients diagnosed with herpes labialis were referred from a dentist with a prescription for acyclovir. Patients had an ongoing outbreak, or were known to be susceptible to recurrent outbreak following dental work. Most patients had previously been treated with one or more of Zovirax® (topical or oral acyclovir), Valtrex® (oral valacyclovir hydrochloride), Famvir® (oral famciclovir), and/or over the counter medications Abreva® (topical 10% docosanol), Zilactin® (topical 10% benzyl alcohol), Novitra® (topical zincum oxydatum 2X) and Campho-Phenique® (topical camphor 10.8% and phenol 4.7%). The patient population received the lip-balm formulation of Example 4. Data to verify treatment outcomes, adverse effects and patient comment was collected by patient survey several months after dispensing the formulation.

One patient population started application of the topical test formulation at a prodrome stage comprising tingling and/or pain, but prior to outbreak. The data for patients who started treatment by topical application of the test formulation at prodrome, prior to full outbreak, is shown in Table 6.

TABLE 6

Clinical Data for Treatment Started at Prodrome.

| Patient No. | Age | Gender F | Gender M | Product Application Average Days Applied | Times/Day | Duration of outbreak Days Prior | During Use |
|---|---|---|---|---|---|---|---|
| 1 | 22 | 0 | 1 | 15.5 | 5.5 | 10.5 | 14 |
| 2 | 48 | 0 | 1 | 9 | 3.5 | 4 | 9 |
| 3 | 51 | 1 | 0 | 1.5 | 3.5 | 2 | 2 |
| 4 | 24 | 1 | 0 | 7.5 | 5.5 | 7 | 6 |
| 5 | 38 | 0 | 1 | 5.5 | 3.5 | 7 | 5 |
| 6 | 50 | 0 | 1 | 7.5 | 5.5 | 10 | 6.5 |
| 7 | 56 | 1 | 0 | 11.5 | 5.5 | 14 | 12 |
| 8 | 20 | 1 | 0 | 7.5 | 3.5 | 6 | 6 |
| 9 | 44 | 0 | 1 | 5.5 | 3.5 | 6 | 1.5 |
| 10 | 53 | 0 | 1 | 3.5 | 3.5 | 5 | 3 |
| 11 | 49 | 1 | 0 | 3.5 | 3.5 | 5 | 1 |
| 12 | 31 | 1 | 0 | 3.5 | 5.5 | 7 | 4 |
| 13 | 36 | 1 | 0 | 1.5 | 1.5 | 9 | 0.5 |
| 14 | 33 | 0 | 1 | 3.5 | 5.5 | 10 | 4 |
| 15 | 45 | 1 | 0 | 1.5 | 3.5 | 8 | 2 |
| 16 | 45 | 1 | 0 | 7.5 | 5.5 | 6.5 | 3 |
| 17 | 52 | 0 | 1 | 3.5 | 3.5 | 10 | 4 |
| 18 | 45 | 0 | 1 | 5.5 | 5.5 | 12 | 2 |
| 19 | 48 | 0 | 1 | 5.5 | 5.5 | 4.5 | 4 |
| 20 | 41 | 0 | 1 | 1.5 | 1.5 | 5 | 3 |
| 21 | 22 | 0 | 1 | 11.5 | 5.5 | 14 | 6 |
| 22 | 59 | 1 | 0 | 3.5 | 1.5 | 6 | 2 |
| 23 | 67 | 1 | 0 | 3.5 | 3.5 | 3 | 3 |
| 24 | 63 | 1 | 0 | 3.5 | 5.5 | 7 | 3 |
| Average | 43.4 | 12.0 | 12.0 | 5.6 | 4.2 | 7.4 | 4.4 |

When topical treatment with the formulation of Example 4 was started at prodrome, the average reduction in duration of outbreak was about three days. Twenty-one of the 24 patients first treated at prodrome preferred the test formulation to other medications. All six of the six patients who reported previous use of Valtrex®, preferred the test formulation. Four of four patients who reported previous use of Zovirax® preferred the test formulation. Patients also generally preferred the test formulation to Abreva® (18), Zilactin® (3), Novitra® (2), and Camphophenique® (1).

Alternatively, another patient population started the test formulation at outbreak; or at first blister, weeping or crusting stage. The data for patients who started treatment by topical application of the test formulation of Example 4 after outbreak is shown in Table 7.

TABLE 7

Clinical Data for Treatment Started after Outbreak

| Patient No. | Age | Gender F | Gender M | Product Application Days Applied | Times/Day | Duration of outbreak Days Prior | During use |
|---|---|---|---|---|---|---|---|
| 1 | 38 | 0 | 1 | 5.5 | 3.5 | 7 | 5 |
| 2 | 55 | 1 | 0 | 7.5 | 5.5 | 7 | 5 |
| 3 | 31 | 0 | 1 | 7.5 | 3.5 | 6 | 7 |
| 4 | 33 | 1 | 0 | 3.5 | 5.5 | 7 | 4 |
| 5 | 13 | 0 | 1 | 3.5 | 7.5 | 6 | 4 |
| 6 | 34 | 0 | 1 | 3.5 | 5.5 | 10 | 6 |
| 7 | 49 | 1 | 0 | 3.5 | 5.5 | 6 | 3 |
| 8 | 31 | 0 | 1 | 3.5 | 5.5 | 6 | 5 |
| 9 | 34 | 1 | 0 | 5.5 | 5.5 | 14 | 6.5 |
| 10 | 25 | 0 | 1 | 7.5 | 5.5 | 7 | 7 |
| 11 | 38 | 1 | 0 | 3.5 | 5.5 | 6 | 3 |
| 12 | 45 | 0 | 1 | 5.5 | 5.5 | 12 | 7 |
| 13 | 54 | 1 | 0 | 9.5 | 3.5 | 10 | 8 |
| 14 | 33 | 1 | 0 | 5.5 | 5.5 | 5 | 2 |
| 15 | 17 | 0 | 1 | 3.5 | 5.5 | 12 | 8 |
| 16 | 38 | 1 | 0 | 3.5 | 5.5 | 8.5 | 3.5 |
| 17 | 18 | 1 | 0 | 5.5 | 5.5 | 14 | 7 |
| 18 | 32 | 1 | 0 | 5.5 | 5.5 | 5 | 3 |
| 19 | 37 | 1 | 0 | 1.5 | 5.5 | 11 | 3 |
| 20 | 9 | 1 | 0 | 3.5 | 3.5 | 7 | 6 |
| 21 | 50 | 0 | 1 | 5.5 | 1.5 | 11 | 6 |
| 22 | 33 | 1 | 0 | 5.5 | 3.5 | 6 | 4 |
| 23 | 53 | 0 | 1 | 5.5 | 3.5 | 14 | 6 |
| 24 | 59 | 0 | 1 | 7.5 | 3.5 | 5 | 3 |
| Average | 35.8 | 13.0 | 11.0 | 5.1 | 4.8 | 8.4 | 5.1 |

When topical treatment with the formulation of Example 4 was started after outbreak, the average reduction in duration of outbreak was about 3.3 days. However, two of 24 patients treated reported no benefit. Twenty of the 24 patients first treated after outbreak preferred the test formulation to other medications. Of four patients that had previously used Valtrex®, three preferred the test formulation. Of two patients that had previously used Zovirax®, one preferred the test formulation. Patients also generally preferred the test formulation to Abreva® (14), Zilactin® (4), Novitra® (4), and Camphophenique® (2).

In general, regardless of whether the topical test medication was started at prodrome or after outbreak, patients made multiple comments that the blisters disappeared, ulcer crusting time appeared to be shortened, and the tingling and pain stopped. In addition, very little to no scabbing occurred.

Example 8

Clinical Survey in HSV-2 Patient

A 23 year old female diagnosed with HSV-2 typically experienced about one recurrent outbreak per year with prodrome symptoms of tingling, soreness, and tenderness around the leg. Outbreak triggers included stress, sunlight, fatigue and hormonal changes. Typical duration of an outbreak was about 7 days. At the first signs of outbreak, including tingling and pain, the patient treated the affected area 3 to 4 times a day for seven days with a topical stick test formulation comprising 4.5 wt % acyclovir and 0.2 wt % 2-deoxy-D-glucose. The formulation employed was similar to that of Table 3, but without sweetener or flavoring. The patient experienced cessation of tingling and pain within 2 days and no full outbreak occurred. The patient reported that the test medication suppressed the HSV outbreak better than Valtrex® when administered twice a day.

The various embodiments described above are provided by way of illustration only and should not be construed to limit the disclosure. Those skilled in the art will readily recognize various modifications and changes that may be made to the present disclosure without following the example embodiments and applications illustrated and described herein, and without departing from the true spirit and scope of the present disclosure, which is set forth in the following claims.

We claim:

1. A topical pharmaceutical composition comprising a therapeutically effective amount of an antiviral compound selected from one or more of the group consisting of acyclovir, or a pharmaceutically acceptable salt or hydrate thereof; and
a therapeutically effective amount of 2-deoxy-D-glucose.

2. The composition of claim 1, wherein the antiviral compound is acyclovir.

3. The composition of claim 1 in a form selected from a lip-balm, stick, cream or ointment.

4. The composition of claim 3 in a lip-balm form.

5. The composition of claim 4, further comprising one or more polyethylene glycols.

6. The composition of claim 5, further comprising one or more sweeteners or flavorings.

7. The composition of claim 6, wherein the sweetener is stevioside.

8. The composition of claim 6, wherein the flavoring is spearmint oil.

9. The composition of claim 2, wherein the composition comprises from about 3 wt % to about 7 wt % of acyclovir and from about 0.1 wt % to about 5 wt % of 2-deoxy-D-glucose.

10. The composition of claim 9, wherein the composition comprises about 5 wt % of acyclovir and about 0.2 wt % of 2-deoxy-D-glucose.

11. A method of treating a herpes viral infection of a patient in need thereof comprising topically administering a pharmaceutical composition comprising a therapeutically effective amount of an antiviral compound selected from the group consisting of acyclovir, or a pharmaceutically acceptable salt thereof; and a therapeutically effective amount of 2-deoxy-D-glucose.

12. The method of claim 11, wherein the antiviral compound is acyclovir.

13. The method of claim 11, wherein the composition is in a form selected from a lip-balm, stick, cream or ointment.

14. The method of claim 13, wherein the composition is in a lip-balm form.

15. The method of claim 12, wherein the composition comprises from about 3 wt % to about 7 wt % of acyclovir and from about 0.1 wt % to about 5 wt % of 2-deoxy-D-glucose.

16. The method of claim 15, wherein the topical comprises about 5 wt % of acyclovir and about 0.2 wt % of 2-deoxy-D-glucose.

17. The method of claim 11, wherein the treatment is for latent infection of herpes simplex type 1 infection.

18. The method of claim 11, wherein the treatment is for latent infection of herpes simplex type 2 infection.

19. The method of claim 11, wherein the infection is an orofacial herpes infection.

20. A method of reducing the duration of a herpes viral infection outbreak in a mammal in need thereof comprising topically administering a pharmaceutical composition comprising a therapeutically effective amount of an antiviral compound selected from the group consisting of acyclovir, or a pharmaceutically acceptable salt thereof; and a therapeutically effective amount of 2-deoxy-D-glucose.

21. The method of claim 20, wherein the antiviral compound is acyclovir.

22. The method of claim 20, wherein the treatment is for latent infection of herpes simplex type 1 infection.

23. The method of claim 20, wherein the treatment is for latent infection of herpes simplex type 2 infection.

24. The method of claim 20, wherein the infection is an orofacial herpes infection.

* * * * *